United States Patent [19]

Kiyota et al.

[11] Patent Number: 4,964,907

[45] Date of Patent: Oct. 23, 1990

[54] SINTERED BODIES AND PRODUCTION PROCESS THEREOF

[75] Inventors: Yoshisato Kiyota; Junichi Ohta; Hiroshi Ohtsubo; Shigeaki Takajo, all of Chiba, Japan

[73] Assignee: Kawasaki Steel Corp., Hyogo, Japan

[21] Appl. No.: 393,765

[22] Filed: Aug. 14, 1989

[30] Foreign Application Priority Data

Aug. 20, 1988 [JP] Japan ................... 63-206703
Aug. 20, 1988 [JP] Japan ................... 63-206705

[51] Int. Cl.$^5$ ............................... C22C 29/12
[52] U.S. Cl. ........................... 75/235; 419/11;
419/19; 419/23; 419/32; 419/36; 419/38;
419/54; 419/57; 75/243
[58] Field of Search ............. 75/243; 419/23, 32,
419/54, 36; 420/41 T

[56] References Cited

U.S. PATENT DOCUMENTS 4,478,790 10/1984 Hüther et al. ................. 419/54
4,721,599 1/1988 Nakamura ..................... 419/23

OTHER PUBLICATIONS

Abstract of Papers, Spring Meeting of Japan Society of Power and Powder Metallurgy, 1988 (pp. 126–127).
Sintering Behavior, Mechanical and Magnetic Properties of Sintered Fe–Si Materials, The International Journal of Power Metallurgy & Powder Technology, vol. 20, No. 4, 1984, American Powder Metallurgy Institute.

*Primary Examiner*—Stephen J. Lechert, Jr.
*Assistant Examiner*—Nina Bhat
*Attorney, Agent, or Firm*—Austin R. Miller

[57] ABSTRACT

A process is provided for the production of a sintered body. The process includes the following consecutive steps: (i) mixing and kneading one or more metal powders and/or one or more alloy powder with a binder into a compound, said metal and alloy powders having an average particle size not greater than 30 μm, (ii) injection-molding the compound into a green body; (iii) debinding the green body to form a debound body; and (iv) subjecting the debound body to first-stage sintering at 1,050°–1,250° C. in a reducing or reduced-pressure atmosphere and then to second-stage sintering at a temperature in a range of 1,100°–1,400° C. which is higher than that of the first-stage sintering. This process can provide sintered Ti bodies and sintered magnetic bodies of the Fe–Si type, which have a density ratio of at least 95%.

5 Claims, No Drawings

SINTERED BODIES AND PRODUCTION PROCESS THEREOF

BACKGROUND OF THE INVENTION

The present invention relates to sintered bodies produced by a powder metallurgical process. In particular, this invention is concerned with sintered bodies such as sintered Ti bodies, sintered magnetic bodies of the Fe-Si type having excellent alternating current (a.c.) characteristics, and their production process.

Prior to this application, one or more of the inventors of this invention and others already have filed "Sintered Fe-Co Type Magnetic Materials and Production Process Thereof (PCT JP89/00537)" and "Stainless Steel Sintered Materials and Production Process Thereof (PCT JP89/00633)".

In these applications, the inventors have described a superior sintered Fe-Co magnetic body which has low C and O contents and high density, a sintered stainless steel body which has high density and high corrosion resistance, and the method of production of these sintered bodies.

Ti has a smaller specific gravity as compared to steel material but its strength is by no means inferior to steel, so that it is employed as a material for a variety of aircraft parts. It is also used for such medical purposes as prostheses and for orthopaedic surgery because it has good compatibility with human tissues, and is without deleterious effects to the human body.

Ti parts have heretofore been formed from Ti ingots. These conventional Ti parts however incur a high production cost and their productivity is low, since their machining yield is low. It has been known that the use of a powder metallurgical process makes it possible to produce sintered Ti bodies at a low cost and with high productivity. Ti is however a very active metal so that the surfaces of its particles tend to be covered with an oxide. This has led to the problem that high-density and low-impurity bodies are difficult to obtain regardless what conventional sintering process is employed. Further, any attempt at using a high-purity Ti powder of low C and O contents inevitably results in a high material cost, whereby the inherent economy of powder metallurgy is impaired.

Injection molding requires a binder in addition to a powdered raw material. It is however difficult to completely remove the binder in a subsequent step, so that the resulting sintered body has high C and O contents. No sintered high-density bodies can therefore be obtained.

Hot isostatic pressing is also recognized as a process for the production of sintered high-density bodies. This process however requires a complex and expensive apparatus and is hence accompanied by the problems of requiring a longer working time and being economically disadvantageous.

Y. Kaneko et al. at Faculty of Science and Engineering, Ritsumeikan Univ. have reported on the injection molding of titanium powder (Abstracts of Papers, Spring Meeting of Japan Society of Powder and Powder Metallurgy, 1988, pp 126 to 127). According to the abstract, a sintered body having a density ratio of 92% was obtained from Ti powder, by injection-molding the powder together with a binder and sintering the molded body at 1300° C. for two hours under a reduced pressure of 0.01 Torr. In addition, it is obvious that this sintered body has a fairly high oxygen content, because the abstract also describes formation of $TiO_2$ based on the results of X-ray diffraction analysis and microscopic observation of the structure.

On the other hand, Fe-Si alloys feature high electrical resistivity among soft magnetic materials. Assisted further by their low core losses, they are employed widely for a.c. applications.

There is however a limitation imposed on the application of sintered bodies of such Fe-Si alloys due to the low compressibility inherited from the hard and brittle properties of the alloys. This tendency is especially remarkable in the case of Fe-Si alloys which contain Si in a proportion of about 3 wt. % or higher.

"Sintering Behavior, Mechanical and Magnetic Properties of Sintered Fe-Si Materials" have been described in the International Journal of Powder Metallurgy & Powder Technology Vol. 20, No. 4, 1984. In this report, the authors described "Fe-Si (sintered) materials that were prepared by varying both the starting Fe powder and the way of Si addition. Water atomized iron powder mixed with pre-alloyed FeSi30 proved to be the most successful."

As a method for improving moldability, injection molding using an organic binder is regarded as a promising candidate because the hardness of a powder is practically immaterial. But when a metal powder is shaped by injection molding and then sintered, there is no method known for eliminating C, which is derived from the organic binder, without extreme oxidation of a highly oxidative element such as Si. It has hence been impossible to provide a sintered body excellent in a.c. magnetic characteristics.

SUMMARY OF THE INVENTION

An object of this invention is to solve the above-described problems and to provide a sintered high-density and low-impurity Ti body by using a conventional vacuum furnace without need for any special apparatus, and also to provide a production process thereof.

Another object of this invention is to provide a sintered magnetic body of the Fe-Si type, said body having excellent a.c. magnetic characteristics, and also a process for producing the above sintered body by using an injection molding method and removing, without extreme oxidation, C derived from an organic binder.

In one aspect of this invention, there is thus provided a process for the production of a sintered body, which comprises the following steps:
  (i) mixing and kneading at least one powder selected from the group which consists of one or more metal powders and one or more alloy powders with a binder into a compound, said metal and alloy powders having an average particle size not greater than 30 μm;
  (ii) injection-molding the compound into a green body;
  (iii) debinding the green body to form a debound body; and
  (iv) subjecting the debound body to first-stage sintering at 1,050°–1,250° C. in a reducing or reduced-pressure atmosphere and then to second-stage sintering at a temperature in a range of 1,100°–1,400° C. which is higher than the temperature of the first-stage sintering.

In another aspect of this invention, there is also provided a process for the production of a sintered Ti body, which comprises the following steps:

(i) mixing and kneading a Ti powder with a binder into a compound, said Ti powder having an average particle size not greater than 30μm;
(ii) injection-molding the compound into a green body;
(iii) debinding the green body to form a debound body; and
(iv) subjecting the debound body to first-stage sintering at 1,050°–1,200° C. in a reduced-pressure not higher than $1\times10^{-3}$ Torr and then to second-stage sintering at a temperature of 1,200°–1,400° C.

In the above processes, it is preferable to adjust the C/O molar ratio of the debound body to 0.5–3.0 before conducting the first-stage sintering.

In a further aspect of this invention, there is also provided a process for the production of a sintered magnetic body of the Fe-Si type, which comprises the following steps:
(i) mixing and kneading at least one powder selected from the group which consists of one or more Fe-Si alloy powders, an Fe powder and a Si powder with a binder into a compound to give a final composition which comprises 1.5–6.5 wt. % of Si and the balance substantially of Fe, said alloy and metal powders having an average particle size of 3–25 μm;
(ii) injection-molding the compound into a green body;
(iii) debinding the green body to form a debound body; and
(iv) subjecting the debound body to first-stage sintering at 1,050°–1,250° C. in a reducing atmosphere or a reduced-pressure atmosphere not higher than 0.1 Torr and then to second-stage sintering at a temperature at least 50° C. higher than the temperature of the first-stage sintering.

It is preferable to adjust the C/O molar ratio of the debound body to 0.5–3.0 before conducting the first-stage sintering. It is also preferable to conduct the second-stage sintering in an inert gas atmosphere of at least 30 atm. In addition, when the second-stage sintering is conducted in an atmosphere of at least 30 atm, the alloy powders and metal powders may preferably have an average particle size of 10–25 μm.

In a still further aspect of this invention, there is also provided a sintered Ti body consisting essentially of up to 0.1 wt. % of C, up to 0.5 wt. % of O, and the balance of Ti and imperative impurities and having a density ratio of at least 95%.

In a still further aspect of this invention, there is also provided a sintered magnetic body of the Fe-Si type consisting essentially of 1.5–6.5 wt. % of Si, up to 0.5 wt. % of O, up to 0.03 wt. % of C, and the balance of Fe and imperative impurities and having a density ratio of at least 95%.

The term "average particle size" as used herein means the particle size at which the cumulative volume from the side of finer particles reaches 50% and is measured by a microtracking particle size analyzer.

On the other hand, the term "density ratio" means the ratio of the bulk density to a corresponding true density and is measured in accordance with the underwater weight measuring method (Archimedean method).

DETAILED DESCRIPTION OF THE INVENTION

A description will first be made of a sintered Ti body according to this invention.

In this invention, a powder having an average particle size not greater than 30 μm is employed as a powdered raw material for the following reasons. Namely, a smaller particle size of a powder results in improved sinterability and an increased density. Average particle sizes greater than 30 μm cannot bring about any high density, and moreover are accompanied by the drawback that the resulting compounds exhibit reduced flowability upon molding, leading to nonuniformly-packed green bodies and hence to sintered bodies having deformations and inferior dimensional accuracy. Accordingly, the upper limit has been set at 30 μm. The preferable average particle size may be not greater than 20 μm.

To impart a desired degree of flowability to the above fine Ti powder so as to permit injection molding, a binder is added and mixed with the fine Ti powder in accordance with this invention, thereby providing a compound for forming.

The forming is effected by injection molding. Use of injection molding makes it possible to form the compound into an intricate shape.

The binder may be a thermoplastic resin and/or a wax. If necessary, one or more of plasticizers, lubricants and debinding promoters may be added further.

Examples of the thermoplastic resin include acrylic resins, polyethylene, polypropylene and polystyrene. Examples of the wax include natural waxes typical of which are bees wax, Japan wax and montan wax, and synthetic waxes typical of which are low molecular weight polyethylene, microcrystalline wax, paraffin wax and the like. One or more of these materials are used.

The plasticizer is selected depending upon the type of resin or wax used as a main ingredient. Specific examples include dioctyl phthalate (DOP) (di (2-ethylhexyl) phthalate), diethyl phthalate (DEP), di-n-butyl phthalate (DBP), diheptyl phthalate (DHP) and the like.

The lubricant may be a higher fatty acid, a fatty acid amide, a fatty acid ester or the like. In some cases, one or more waxes may also be used as the lubricant.

The debinding promoter may be a sublimable substance such as camphor.

In injection molding, the proportion of the binder may preferably range from 40 vol. % to 50 vol. % based on the compound which is the mixture of the Ti power and binder.

After forming, debinding is conducted. In a conventional debinding method, the green body thus formed is heated at a predetermined rate to a desired temperature and is then maintained at the same temperature, both in a non-oxidizing atmosphere so as to remove the binder. Here, any excessively high heating rate leads to development of cracks and/or blisters in the resulting debound body. Therefore, the heating rate is controlled preferably within a range of 5°–20° C./hr.

Subsequent to the debinding, sintering is conducted to achieve densification. The binder is not removed completely by the debinding, and a certain portion of the binder still remains in the debound body even after the debinding. By promoting the reaction between the carbon of the remaining binder and the oxygen in oxide films formed on the surfaces of individual Ti particles, the contents of C and O as impurities in the sintered final body are reduced as much as possible. The C/O molar ratio can be adjusted to an optimum value by controlling the degree of removal of the binder in the course of the debinding or by preheating the thus-debound body before its sintering while controlling the preheating temperature and/or the oxygen potential in the preheating atmosphere. As a result, the contents of C and O can be reduced.

The debound body is thereafter sintered first at 1,050°-1,200° C. in a vacuum of $1\times10^{-3}$ Torr or lower and then at 1,200°-1,400° C., whereby a sintered high-density body having a density ratio of 92% or higher can be obtained.

Ti powder which is an essential raw material for the practice of this invention is very active and has strong affinity with oxygen. Its surface is usually covered with an oxide, which can hardly be reduced in a hydrogen atmosphere employed in a conventional sintering step.

However, this invention can easily accelerate reduction of the oxide by using carbon, which is contained in the debound body, while proceeding with the sintering in a reduced-pressure atmosphere.

Sintering begins to take place from the points of contact among particles and proceeds through solid-phase diffusion of atoms. So long as particle surfaces are covered with an oxide however, diffusion of atoms is impaired so that densification does not proceed and no high-density sintered body can be obtained. It is hence indispensable to reduce the oxide on the particle surfaces in order to obtain a high density.

For this purpose, sintering is effected in a reduced-pressure atmosphere. If the pressure of the atmosphere exceeds $1\times10^{-3}$ Torr, the reducing reaction of the oxide does not proceed smoothly. Thus the upper limit of the pressure of the atmosphere for the first-stage sintering is set at $1\times10^{-3}$ Torr.

Although the reducing reaction of the oxide can proceed using carbon contained in the debound body as described above, it is preferable to suitably adjust the C/O molar ratio in the debound body before sintering. Because, the reduction of C and O contents in the sintered body can be achieved by allowing the following reactions to proceed:

$$C + O \rightarrow CO$$

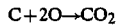

$$C + 2O \rightarrow CO_2$$

Unsuitable C/O molar ratio results in a sintered body in which C or O still remains excessively. C/O molar ratio smaller than 0.5 leads to a sintered body having an O content higher than 0.5 wt. %, so that it is difficult to achieve densification of the sintered body. On the other hand, a C/O molar ratio greater than 3.0 results in a sintered body having a C content higher than 0.1 wt. %, so that the sintered body is hard and brittle. It is therefore desirable to control within the range of 0.5-3.0 the C/O molar ratio of the debound body before sintering.

The preferable temperature range for first-stage sintering in a reduced-pressure atmosphere is limited to 1,050°-1,200° C. because temperatures lower than 1,050° C. cannot achieve sufficient reduction of the oxide so that some of the oxide still remains and impairs the subsequent sintering. Furthermore, C also remains at a high level so that there is a potential problem of carbide formation. Accordingly, the lower limit has been set at 1,050° C.

On the other hand, 1,200° C. has been chosen as the upper limit for the following reasons. Temperatures higher than this upper limit lead to abrupt closure of pores so that CO and $CO_2$ gases remain inside the sintered body. As a result, more impurities are contained in the sintered final body. The upper limit of the first-stage sintering temperature has been set at 1,200° C.

Thereafter, the sintered body is heated to 1,200°-1,400° C. and is maintained at this temperature to achieve high densification. At temperatures lower than 1,200° C., the velocity of diffusion of Ti is too slow to achieve high densification. As a result, many pores still remain and the resultant sintered body has inferior mechanical properties and chemical stability. The lower limit has therefore been set at 1,200° C.

Temperatures higher than 1,400° C. cannot bring about marked effects for the increase of density because pore shrinkage by solid-phase sintering has already been finished. In addition, refractories and heating elements in the vacuum furnace undergo substantial burnout so that the economy is impaired. Therefore, the upper limit has been set at 1,400° C.

It is preferable to conduct the second-stage sintering, which is conducted at 1,200°-1,400° C., in an atmosphere of a high-purity inert gas or under a reduced-pressure atmosphere in order to avoid mixing of impurities.

As has been described above, the process of this invention for the production of a sintered Ti body is a two-stage sintering process which comprises in combination reduced-pressure sintering at a relatively low temperature for a provisional adjustment of the C/O molar ratio of a debound body and subsequent sintering at a relatively high temperature for densification. This two-stage sintering process has made it possible to produce a sintered high-density and low-impurity body in a conventional vacuum furnace.

Next, the sintered Ti body according to this invention is a sintered body of a Ti powder, which consists essentially of up to 0.1 wt. % of C, up to 0.5 wt. % of O, and the balance of Ti and imperative impurities and has a density ratio of at least 95%.

As already mentioned above, a Ti powder is very active and has high affinity with oxygen. Their surfaces therefore tend to be covered with an oxide. This Ti oxide however prevents densification of a sintered body. It is therefore necessary to reduce the oxide to lower the O content in the sintered body. However, it is difficult to conduct the reduction in hydrogen atmosphere. Reduction by carbon is therefore needed. As a corollary to this, the sintered Ti body has a high C content. Further, a process involving a powder metallurgical method, especially injection molding uses an organic compound as a binder for a Ti powder. Since this organic compound cannot be removed completely even after debinding, this process results in the formation of a sintered Ti body having a high C content.

For these reasons, it has heretofore been impossible to obtain a sintered Ti body which is low in both C and O contents but is high in density.

The C content is limited to 0.1 wt. % or lower in the sintered Ti body of this invention, because C contents higher than 0.1 wt. % tend to result in a sintered body which is hard and brittle. On the other hand, the O content is limited to 0.5 wt. % or lower because O contents higher than 0.5 wt. % render the densification of a sintered body difficult. By controlling the C and O contents of a sintered Ti body within their respective ranges specified by the present invention, it is possible to achieve a density ratio of 95% or higher.

In accordance with the production process of this invention, sintered Ti bodies of this invention can be obtained.

A description will next be made of the process of this invention for the production of a sintered magnetic body of the Fe-Si type. According to the production process of this invention, a metal powder is mixed and kneaded with an organic binder, followed by injection molding, debinding and sintering. In particular, a principal feature of the process of this invention resides in the adoption of injection molding in place of compression forming which has generally been relied upon. In compression forming, the powdered raw material is limited to a coarse powder having low sinterability. Compared to compression forming, injection molding is advantageous in that a fine powder having high sinterability can be used. This has made it possible to improve the conventional low magnetic characteristics.

The present inventors have found that the magnetic characteristics of a sintered body are closely correlated to the particle size of the powdered raw material. The average particle size of the powdered raw material governs the density of the sintered body. Average particle sizes in excess of a predetermined upper limit cannot provide any sintered body according to this invention.

Although the particle size of the powdered raw material varies depending on the manner of sintering, the average particle size is generally required to fall within a range of 3–25 μm. First, an average particle size of 3–9 μm is preferred when sintering is conducted by usual heating alone. When pressure-assisted sintering involving simultaneous heating and gas pressurization is applied, 10–25 μm is preferred. When sintering is effected only by heating, a greater average particle size results in a lower density ratio of the sintered body. Average particle sizes greater than 9 μm cannot give the density ratio of 95%. Further, average particle sizes greater than 25 μm cannot attain the density ratio of 90%. However, so long as the density ratio of the sintered body is greater than 90%, the pores of the sintered body are in the form of closed pores so that the density ratio can be increased to 95% or higher by pressure-assisted sintering.

As a matter of fact, a significant improvement can be observed in the density ratio upon pressure-assisted sintering where the average particle size is 10 μm or greater, so that a density ratio rather greater than that available from the use of a powder having an average particle size smaller than 10 μm may be obtained.

On the other hand, average particle sizes greater than 25 μm can by no means achieve any density ratio of 95% or greater, thereby failing to provide a sintered body according to this invention. The upper limit of the average particle size has therefore been set at 25 μm. Further, powders having an average particle size smaller than 3 μm are expensive and hence uneconomical. These powders have therefore been excluded.

A description will next be made of conditions for the sintering.

It is indispensable to conduct the sintering in two stages.

The first-stage sintering must be conducted in a hydrogen-containing gas, which is a reducing atmosphere, or in a reduced-pressure atmosphere of 0.1 Torr or lower. Otherwise, surface oxygen of the powdered raw material and carbon derived from the remaining binder cannot be eliminated and no sintered high-purity body can hence be obtained. It is also necessary to conduct the first-stage sintering at 1,050°–1,250° C. If the sintering temperature is lower than the lower limit of this range, the reaction which is supposed to take place between the atmosphere and the powdered raw material for the elimination of impurities does not proceed effectively. On the other hand, sintering temperatures higher than the upper limit allow interparticle sintering of the powder to proceed faster than the reaction for the elimination of the impurities so that the impurities cannot be eliminated. Since these impurities are eliminated as water vapor or carbon dioxide gas, the loss of gas flow pores poses a serious problem. Special care must be paid in this regard because a green body is formed of fine particles and its flow pores are inherently small. In addition, the temperature of the first-stage sintering is the temperature at which the progress of sintering begins to accelerate. Since this temperature also varies depending on the particle size of the powdered raw material, it is desirable to choose the temperature of the first-stage sintering on a lower side when the average particle size is small and on a higher side when the average particle size is large, both from the temperature range of the present invention.

The sintering period is the time required until the contents of C and O reach equilibrium at the sintering temperature employed. It is usually in a range of from 20 minutes to 4 hours. The sintering time can be easily determined by conducting several trial experiments.

The second-stage sintering of this invention will next be described.

The second-stage sintering no longer requires any reactive gas because it is applied to densify the sintered body which has been subjected to purification and pore closure in the first-stage sintering step. Therefore, the atmosphere gas may preferably be limited to an inert gas. Further, the temperature must be at least 50° C. higher than the sintering temperature of the first-stage sintering.

The lower limit of the temperature has been set at a temperature at least 50° C. higher than the first-stage sintering temperature, because the first-stage sintering temperature is set at the temperature at which the sintering speed begins to accelerate and is not high enough for densification. When a reduced-pressure atmosphere is used in the first-stage sintering step, a compositional distribution occurs in the surface of the resultant sintered body because of differences in vapor pressure among the constituent elements. Even in an atmosphere of a reducing gas, a compositional distribution may also occur between the surface of a sintered body or each particle, said surface being exposed to the gas, and the inside thereof. This compositional distribution occurs by differences in atomic diffusion velocity within the sintered body. It is therefore necessary to allow the homogenization treatment to proceed promptly at a temperature at least 50° C. higher than the temperature of the first-stage sintering, namely, in a temperature range capable of realizing a higher diffusion velocity in an atmosphere of atmospheric pressure of higher, at which the constituent elements do not evaporate, or in an atmosphere in which absolutely no chemical reaction takes place.

The upper limit of the second-stage sintering temperature is the temperature at which the crystal grain size does not become coarse beyond necessity and no melting begins to take place. The more suitable temperature range is 1,200°–1,350° C.

Even when pressure-assisted sintering is conducted in the above second-stage step, the lower limit of the temperature should be at least 50° C. higher than the temperature of the first-stage sintering. This lower limit temperature is the temperature which the sintering velocity begins to increase, and is correlated to the temperature set for the first-stage sintering. Above this temperature, pressure-assisted sintering becomes effective. Further, as has been described above, it is necessary to allow a homogenization treatment to proceed promptly in this step in order to eliminate the compositional distribution as occurred in the first-stage sintering. Pressure-assisted sintering also requires a similar upper limit temperature to pressureless sintering. The pressure required for pressurization ranges from 30 atm to 150 atm. Pressures lower than 30 atm cannot bring about any significant difference compared to pressureless sintering, while the use of a gaseous medium higher than 150 atm leads to a tremendous increase in the initial cost.

The period of the second-stage sintering is the time required until the sintered density and chemical compositional distribution reach equilibrium at the sintering temperature employed. It generally ranges from 20 minutes to 2 hours. It can be easily chosen through several trial experiments.

By limiting the sintering method as described above, it is possible for the first time to economically produce sintered Fe-Si bodies of high magnetic characteristics by virtue of injection molding.

The starting powdered raw material, which constitutes the powdered raw material of this invention, is used after adjusting its particle size to a suitable level by sifting or grinding it subsequent to its formation by the high-pressure water atomizing method, the reducing process, the carbonyl process or the like. As the powdered raw material in this invention, such starting powdered raw materials can be used either singly or in combination. Regarding the purity of the powdered raw material, it may contain impurities other than C and O, which can be eliminated in the course of sintering, at practically-ignorable level. In general, powders containing Fe and Si in a total proportion of 97-99 wt. % can be used.

The powdered raw material is mixed and kneaded with a binder into a compound, which is then shaped by a known injection molding method. In particular, injection molding is effective for parts of an intricate shape.

Usable binders are similar to those already discussed above with respect to sintered Ti bodies.

The amount of the binder to be added may range from 40 vol. % to 60 vol. % of the total volume (the remaining volume corresponds to the starting metal powder). This can be adjusted in view of the forming readiness of the compound obtained the debinding property of the green body obtained.

A batchwise or continuous kneader can be used for the mixing and kneading of the metal powder and the binder. After mixing and kneading, the compound is granulated by means of a pelletizer, a granulator or the like so that a forming feed-stock can be obtained.

The forming feed-stock can be formed by means of a conventional injection molding machine for plastics.

The green body thus obtained is then subjected to a debinding treatment in atmosphere or in a surrounding gas.

After the debinding treatment, sintering is conducted as described above so as to achieve reduction of C and O contents and high densification.

In addition, the C and O contents of the sintered final body may be adjusted as needed. The C and O contents may be increased or decreased by adjusting the molar C/O ratio of the debound body. The C content can be reduced by making the molar C/O ratio smaller, while the O content can be lowered by making the molar C/O ratio greater.

It is preferable to adjust the molar C/O ratio to 0.5–3.0, more preferably to 0.6–1.0, because these ranges can easily provide sintered bodies of low contents of C and O in the range of this invention.

Adjustment of the C/O molar ratio can be achieved, for example, by controlling the C and O contents in the powdered raw material, by increasing or decreasing the degree of debinding, and/or by applying an oxidation treatment after the debinding. Reduction of the overall level of the C and O contents, said level being equivalent to the product of the C content and the O content, can be effected by modifying the atmosphere for the first-stage sintering. When a reduced-pressure atmosphere is used, this can be achieved by reducing the pressure. When a reducing atmosphere is used, this can be attained by improving the purity of the atmosphere gas.

A description will next be made of the sintered magnetic body of the Fe-Si type according to this invention. The sintered magnetic body of the Fe-Si type consists essentially of 1.5–6.5 wt. % of Si, up to 0.5 wt. % of O, up to 0.03 wt. % of C, and the balance of Fe and imperative impurities and has a density ratio of at least 95%.

The composition of the sintered body of this invention has been limited as described above for the following reasons.

Si: 1.5–6.5 wt. %

When added to Fe, Si can improve the electrical resistivity. Proportions smaller than 1.5 wt. % are however too little to draw out its effect to a significant extent. In addition, Si can also improve magnetic permeability. Its permeability-improving effect however drops abruptly when the proportion of Si exceeds 6.5 wt. %. The proportion of Si has therefore been limited to 1.5–6.5 wt. %.

O: up to 0.5 wt. %; C: up to 0.03 wt. %

C and O give deleterious influence to magnetic characteristics, especially to coercive force (Hc) and maximum magnetic permeability ($\mu$max).

However, when an element highly susceptible to oxidation such as Si is contained, it is practically impossible to simultaneously reduce the contents of O and C, which have been derived respectively from the powdered raw material and the organic binder added to convert the powdered raw material into the compound suitable for injection molding, in the sintering atmosphere. The principal object was therefore placed on the reduction of the content of C which adversely affects magnetic characteristics in particular. Namely, magnetic characteristics undergo substantial deteriorations when the content of C exceeds 0.03 wt. %. Therefore, the upper limit of the C content has been set at 0.03 wt. %.

On the other hand, magnetic characteristics are also deteriorated significantly when the O content exceeds 0.5 wt. %. Therefore, the upper limit of the O content has been set at 0.5 wt. %. It is preferable to limit the contents of O and C to 0.1 wt. % or less and 0.03 wt. % or less, respectively.

Further, when the O content is in the range of 0.03 wt. % to 0.5 wt. %, the sintered body which has content of not more than 0.03 wt. % is easily obtained. Therefore an O content of 0.03 wt. % to 0.5 wt. % is preferable in industrial processes.

Density Ratio: at least 95%

Magnetic flux density is proportional to the density ratio of the sintered body. When the density ratio is smaller than 95%, the magnetic flux density is reduced substantially so that the resultant sintered body may not be found superior to a sintered body obtained by compression molding which is a competitive forming method.

Accordingly, the lower limit of the density ratio has been set at 95%.

Introduction of the above limitations has made it possible for the first time to obtain sintered Fe-Si bodies of this invention, which have excellent magnetic characteristics.

EXAMPLES

This invention will hereinafter be described specifically on the basis of the following examples.

EXAMPLES 1-3 & COMPARATIVE EXAMPLES 1-3

Ti powders whose average particle sizes are shown in Table 1 were provided as powdered raw materials. Each of the Ti powders was added and mixed with a thermoplastic resin and a wax as binders. The resultant mix was kneaded into a compound by a dispersion mixer.

The compound was granulated to obtain a forming feed-stock.

The forming feed-stock was formed into a plate-like green body 2 mm thick by means of an injection molding machine. The green body was heated to 600° C. at a heating rate of 10° C./hr in a nitrogen atmosphere. Thereafter, the temperature and the oxygen potential in the atmosphere were controlled to adjust the C/O molar ratio in the body to 0.5-1.0.

The thus-debound body was maintained for at least 1 hour in a reduced pressure atmosphere ($<10^{-3}$ Torr) at the temperature given in Table 1, and was then heated to 1,300° C., at which it was maintained for 3 hours.

After cooling, its density ratio was determined from its density measured by the Archimedean method and a measurement datum of its true density. Further, the contents of C and O in the sintered body were analyzed.

The results are summarized in Table 1.

Examples 1 and 2 gave sintered bodies of high density and low impurity because the average particle size of the powdered raw material was 10 μm and the first-stage sintering temperature was controlled at 1,080° C. or 1,150° C.

In Example 3, the average particle size of the powdered raw material was 25 μm and hence greater compared with Examples 1 and 2. Accordingly, Example 3 gave a sintered body having still lower C and O contents although the density ratio was 95%.

In Comparative Example 1, the first-stage sintering temperature was as low as 1,000° C. The sintering was switched to high-temperature sintering probably before the elimination of C and O had proceeded sufficiently. This seems to be responsible to the high C and O contents of the sintered final body.

In Comparative Example 2, the first-stage sintering temperature was as high as 1,250° C. This appears to have promoted the closure of pores, whereby CO and $CO_2$ gases were probably trapped. This seems to be responsible for the high C and O contents of the sintered final body.

In Comparative Example 3, the first-stage sintering temperature was 1,150° C. and the elimination of C and O proceeded. However, the powdered raw material had the average particle size of 35 μm and was a coarse powder. Comparative Example 3 therefore failed to provide any sintered body of high density.

EXAMPLES 4-5 & COMPARATIVE EXAMPLES 4-5

In a manner similar to Examples 1-3, each green body was formed and then subjected to debinding. Thereafter, the C/O molar ratio in the green body was adjusted to 0.2-4.0.

The thus-debound body was then sintered in a similar manner as in Examples 1-3, followed by the determination of the density ratio and the analyses of the C and O contents in the resultant sintered body.

The results are summarized in Table 2.

Examples 4 and 5 gave sintered bodies of high density and low impurity, because the C/O molar ratios fell within the range specified in this invention.

In Comparative Example 4, the C/O molar ratio was unduly small. It appears that the O content was too high and an oxide remained and impaired the attempted density increase.

In Comparative Example 5, the C/O molar ratio was unduly large. It appears that the content of remaining C was too high and unreacted C still remained at the high level in the sintered final body even after the reducing reaction.

TABLE 1

|  | Average particle size of powdered raw material, m | C/O molar ratio in debound body | First-stage sintering temperature, °C. | Density ratio of sintered body, % | C content in sintered body, wt % | O content in sintered body, wt % |
| --- | --- | --- | --- | --- | --- | --- |
| Example 1 | 10 | 0.7 | 1080 | 96.0 | 0.05 | 0.31 |
| Example 2 | 10 | 0.7 | 1150 | 96.4 | 0.04 | 0.28 |
| Example 3 | 25 | 0.8 | 1150 | 95.2 | 0.03 | 0.25 |
| Comp. Ex. 1 | 10 | 0.7 | 1000 | 90.1 | 0.27 | 0.43 |
| Comp. Ex. 2 | 10 | 0.7 | 1250 | 90.3 | 0.26 | 0.51 |
| Comp. Ex. 3 | 35 | 0.5 | 1150 | 89.5 | 0.08 | 0.34 |

TABLE 2

|  | C/O molar ratio in debound body | Density ratio of sintered body % | C Content in sintered body, wt % | O Content in sintered body, wt % |
| --- | --- | --- | --- | --- |
| Example 4 | 1.2 | 96.3 | 0.05 | 0.23 |
| Example 5 | 2.4 | 95.2 | 0.02 | 0.22 |
| Comp. Ex. 4 | 0.2 | 88.4 | 0.05 | 0.54 |

TABLE 2-continued

| | C/O molar ratio in debound body | Density ratio of sintered body % | C Content in sintered body, wt % | O Content in sintered body, wt % |
|---|---|---|---|---|
| Comp. Ex. 5 | 4.0 | 92.1 | 0.31 | 0.11 |

By using as a raw material a powder having an average particle size not greater than 30 μm, conducting C/O adjustment of a green body in a conventional vacuum furnace before sintering and applying in combination low-temperature sintering under reduced pressure and high-temperature sintering, this invention has made it possible to produce sintered Ti bodies of low C and O contents and high density. It is hence possible to produce sintered Ti parts at a low cost and excellent productivity.

EXAMPLES 6–21 & COMPARATIVE EXAMPLES 6–12

Each of the powdered raw materials shown in Table 3 was added with its corresponding binder also given in Table 3. After kneading the resultant mixture into a compound by a dispersion mixer, the compound was granulated to prepare an injection-molding feed-stock. The feed-stock was then formed into a ring-shaped green body having an outer diameter of 53 mm, an inner diameter of 41 mm and a height of 5 mm by an injection molding machine. The green body was then heated to 600° C. at a rate of 5° C./hr in nitrogen gas, at which it was maintained for 30 minutes to apply a debinding treatment.

Next, the debound body was then subjected to first-stage sintering and second-stage sintering under the corresponding conditions indicated in Table 3. The chemical composition and density ratio of the thus-obtained sintered body were measured. Further, a winding was applied to the specimen thus prepared, and its magnetic characteristics and electrical resistivity were measured by an automatic flux measuring and recording instrument. The results are also given in Table 3.

In each of Run Nos. 1-1 to 1-5 given in Table 3, the contents of C and O in the debound body were adjusted by controlling the heating temperature in a range of 350°–650° C. in a hydrogen atmosphere whose dew point was 0° C., followed by first-stage sintering and second-stage sintering.

It is appreciated from Run Nos. 1-1 to 1-5 of Table 3 that magnetic characteristics were deteriorated when the contents of C and O exceeded 0.03 wt. % and 0.5 wt. % respectively (Comparative Examples 6 and 7). Further, when the content of O was unduly low (Comparative Example 6), it was unable to lower the content of C so that magnetic characteristics were deteriorated extremely. However, excellent magnetic characteristics were obtained when the contents of C and O were within their corresponding ranges specified in this invention (Examples 6–10).

When the temperature of the first-stage sintering was higher than the upper limit specified in this invention (Comparative Example 9) or lower than the lower limit defined in this invention (Comparative Example 10), the content of C was higher than the upper limit defined in this invention so that magnetic characteristics were deteriorated.

When the temperature of the second-stage sintering was not higher by at least 50° C. than the temperature of the first-stage sintering (Comparative Example 8), the low density ratio was only available so that excellent magnetic characteristics were not obtained.

When pressure-assisted sintering is effected in the second-stage sintering, no effects can be brought about when the pressure is lower than 30 atm (Comparative Example 11). Further, when the average particle size of the raw material exceeds 25 μm (Comparative Example 12), no advantage can be brought about. On the other hand, particle sizes smaller than 10 μm (Example 16) cannot draw out the effects of this invention fully.

The density ratios of the sintered bodies subjected to pressure-assisted sintering at 30 atm or higher (Invention Examples 16–21) were all found higher than those of the bodies sintered under normal pressure (Examples 6–15).

TABLE 3

| Run No. | Powdered raw material Constituent powder Average particle size, μm, in parentheses | Average particle size, μm | Binder Amount added, wt %, in parentheses | First-stage sintering Atmosphere | Temperature, °C. | Second-Stage sintering Atmosphere | Temperature, °C. |
|---|---|---|---|---|---|---|---|
| 1-1 | Carbonyl Fe powder | 4.9 | Wax type (10) | 0.001 Torr | 1155 | 1 atm Ar | 1300 |
| 1-2 | (4.8) + | 4.8 | Wax type (10) | 0.001 Torr | 1155 | 1 atm Ar | 1300 |
| 1-3 | ground Fe-44%Si | 4.9 | Wax type (10) | 0.001 Torr | 1155 | 1 atm Ar | 1300 |
| 1-4 | powder (6.9) | 4.9 | Wax type (10) | 0.001 Torr | 1155 | 1 atm Ar | 1300 |
| 1-5 | | 4.8 | Wax type (10) | 0.001 Torr | 1155 | 1 atm Ar | 1300 |
| 1-6 | | 4.9 | Wax type (10) | 0.001 Torr | 1155 | 1 atm Ar | 1300 |
| 1-7 | | 4.9 | Wax type (10) | 0.001 Torr | 1155 | 1 atm Ar | 1300 |
| 1-8 | | 4.8 | Wax type (10) | 0.001 Torr | 1155 | 1 atm Ar | 1300 |
| 1-9 | | 5.0 | Wax type (10) | 0.001 Torr | 1155 | 1 atm Ar | 1300 |
| 1-10 | | 4.9 | Wax type (10) | $H_2$ | 1200 | $H_2$ | 1275 |
| 1-11 | | 4.9 | Wax type (10) | 0.001 Torr | 1155 | 1 atm Ar | 1180 |
| 2-1 | Atomized Fe—Si powder | 9.5 | Resin type (9) | 0.001 Torr | 1000 | 1 atm Ar | 1300 |
| 2-2 | Atomized Fe—Si powder | 9.5 | Resin type (9) | 0.001 Torr | 1100 | 1 atm Ar | 1300 |
| 2-3 | Atomized Fe—Si powder | 9.5 | Resin type (9) | 0.001 Torr | 1200 | 1 atm Ar | 1300 |
| 2-4 | Atomized Fe—Si powder | 9.5 | Resin type (9) | 0.001 Torr | 1300 | 1 atm Ar | 1300 |
| 3-1 | Atomized Fe—Si powder | 9.5 | Resin type (9) | 0.001 Torr | 1145 | 150 atm Ar | 1300 |
| 3-2 | Atomized Fe—Si powder | 11.3 | Resin type (9) | 0.001 Torr | 1145 | 150 atm Ar | 1300 |
| 3-3 | Atomized Fe—Si powder | 18.2 | Resin type (9) | 0.001 Torr | 1145 | 150 atm Ar | 1300 |
| 3-4 | Atomized fe—Si powder | 18.2 | Resin type (9) | 0.001 Torr | 1145 | 25 atm Ar | 1300 |
| 3-5 | Atomized Fe—Si powder | 18.2 | Resin type (9) | 0.001 Torr | 1145 | 30 atm Ar | 1300 |
| 3-6 | Atomized Fe—Si powder | 21.9 | Resin type (9) | 0.001 Torr | 1145 | 150 atm Ar | 1300 |
| 3-7 | Atomized Fe—Si powder | 28.2 | Resin type (9) | 0.001 Torr | 1145 | 150 atm Ar | 1300 |
| 3-8 | Same as Nos. 1-1 to 1-11 | 4.9 | Resin type (9) | 0.001 Torr | 1145 | 150 atm $N_2$ | 1300 |

TABLE 3-continued

| Run No. | Chemical composition of sintered body Si content, wt % | O content, wt % | C content, wt % | Density ratio, % | Magnetic characteristics B$_{20}$, kG | Hc, Oe | $\mu_{max}$ | Electrical resistivity, $\mu\Omega$ cm | Remarks |
|---|---|---|---|---|---|---|---|---|---|
| 1-1 | 3.5 | 0.44 | 0.01 | 95.8 | 14.2 | 0.4 | 3300 | 48 | Example 6 |
| 1-2 | 3.5 | 0.34 | 0.02 | 95.6 | 14.2 | 0.4 | 3200 | 48 | Example 7 |
| 1-3 | 3.5 | 0.33 | 0.03 | 95.7 | 14.2 | 0.7 | 3000 | 48 | Example 8 |
| 1-4 | 3.5 | 0.02 | 0.11 | 95.7 | 13.8 | 1.5 | 1300 | 47 | Comp. Ex. 6 |
| 1-5 | 3.5 | 0.45 | 0.02 | 95.6 | 13.9 | 0.7 | 2500 | 49 | Comp. Ex. 7 |
| 1-6 | 3.5 | 0.05 | 0.03 | 95.7 | 14.2 | 0.6 | 3100 | 48 | Example 9 |
| 1-7 | 3.5 | 0.10 | 0.02 | 95.7 | 14.2 | 0.4 | 3200 | 48 | Example 10 |
| 1-8 | 1.7 | 0.55 | 0.02 | 95.3 | 15.2 | 0.4 | 2300 | 31 | Example 11 |
| 1-9 | 6.3 | 0.38 | 0.02 | 95.9 | 12.8 | 0.2 | 7200 | 87 | Example 12 |
| 1-10 | 3.5 | 0.32 | 0.02 | 95.3 | 14.2 | 0.4 | 3100 | 48 | Example 13 |
| 1-11 | 3.5 | 0.30 | 0.02 | 92.8 | 13.5 | 1.0 | 1800 | 50 | Comp. Ex. 8 |
| 2-1 | 4.5 | 0.10 | 0.12 | 95.3 | 13.0 | 1.6 | 1200 | 58 | Comp. Ex. 9 |
| 2-2 | 4.5 | 0.37 | 0.02 | 95.3 | 13.4 | 0.4 | 3400 | 61 | Example 14 |
| 2-3 | 4.5 | 0.41 | 0.02 | 95.6 | 13.4 | 0.4 | 3300 | 59 | Example 15 |
| 2-4 | 4.5 | 0.45 | 0.04 | 95.4 | 13.1 | 0.8 | 2300 | 59 | Comp. Ex. 10 |
| 3-1 | 3.3 | 0.35 | 0.02 | 96.7 | 14.4 | 0.3 | 3800 | 42 | Example 16 |
| 3-2 | 3.3 | 0.31 | 0.02 | 97.8 | 14.6 | 0.3 | 4500 | 42 | Example 17 |
| 3-3 | 3.3 | 0.29 | 0.01 | 98.5 | 14.7 | 0.3 | 5100 | 42 | Example 18 |
| 3-4 | 3.3 | 0.25 | 0.02 | 94.5 | 14.1 | 0.7 | 2800 | 43 | Comp. Ex. 11 |
| 3-5 | 3.3 | 0.29 | 0.01 | 96.1 | 14.4 | 0.4 | 3500 | 42 | Example 19 |
| 3-6 | 3.3 | 0.25 | 0.01 | 97.5 | 14.6 | 0.3 | 5000 | 42 | Example 20 |
| 3-7 | 3.3 | 0.24 | 0.01 | 89.0 | 13.2 | 1.2 | 1400 | 46 | Comp. Ex. 12 |
| 3-8 | 6.2 | 0.37 | 0.02 | 98.3 | 13.5 | 0.2 | 4900 | 85 | Example 21 |

This invention can provide sintered Fe-Si magnetic bodies of excellent a.c. magnetic characteristics by using an injection molding method and eliminating organic-binder-derived C without extreme oxidation.

We claim:

1. A process for the production of a sintered body, which comprises the following steps:
   (i) mixing and kneading at least one powder selected from the group which consists of one or more metal powders and one or more alloy powders with a binder into a compound, said metal and alloy powders having an average particle size not greater than 30 μm;
   (ii) injection-molding the compound into a green body;
   (iii) debinding the green body to form a debound body; and
   (iv) subjecting the debound body to first-stage sintering at 1,050°–1,250° C. in a reducing or reduced-pressure atmosphere and then subjecting the body to second-stage sintering at a temperature in the range of 1,100°–1,400° C., which temperature is higher than that of the first-stage sintering.

2. The process as claimed in claim 1, further comprising the step of adjusting the C/O molar ratio of the debound body before conducting the first-stage sintering, and wherein the first-stage sintering is conducted in a reduced-pressure atmosphere.

3. The process as claimed in claim 1, wherein the powder which is mixed and kneaded as the metal powder with the binder is a Ti powder, said Ti powder having an average particle size not greater than 30 μm, and wherein the first-stage sintering step is conducted at 1,050°–1,200° C. in an atmosphere having a pressure not higher than $1 \times 10^{-3}$ Torr, and wherein the second-stage sintering step is conducted at 1,200°–1,400° C.

4. The process as claimed in claim 3, further comprising the step of adjusting the C/O molar ratio of the debound body to 0.5–3.0 before conducting the first-stage sintering step.

5. A sintered Ti body consisting essentially of Ti, C and O the amount being up to 0.1 wt. % of C, up to 0.5 wt. % of O, and the balance of Ti and imperative impurities and having a density ratio of at least 95%.

* * * * *